United States Patent [19]

Muccitelli et al.

[11] Patent Number: 4,883,566
[45] Date of Patent: Nov. 28, 1989

[54] ELECTRODE ASSEMBLY FOR IN-SITU MEASUREMENT OF ELECTROLYTIC CONDUCTIVITY OF BOILER WATER

[75] Inventors: John A. Muccitelli, Feasterville; Nancy A. Feldman, Trevose, both of Pa.

[73] Assignee: Betz Laboratories, Inc., Trevose, Pa.

[21] Appl. No.: 203,779

[22] Filed: Jun. 7, 1988

[51] Int. Cl.[4] ...................... G01N 27/02; G01N 27/26
[52] U.S. Cl. .................................... 204/1 T; 204/400; 324/439
[58] Field of Search .................. 204/400, 1 T; 324/439

[56] References Cited

U.S. PATENT DOCUMENTS 4,636,292 1/1987 Fejes et al. ......................... 204/404

OTHER PUBLICATIONS

Stevens, An Introduction to Zirconia, Jun. 1983, Published by Magnesium Elektron Ltd., p. 9.

Primary Examiner—T. Tung
Assistant Examiner—David G. Ryser
Attorney, Agent, or Firm—Caesar, Rivise, Bernstein, Cohen & Pokotilow, Ltd.

[57] ABSTRACT

An electrode assembly and a method of electrically insulating the electrode assembly for in-situ measurement of electrolytic conductivity of boiler or other hot alkaline or neutral water, the electrode assembly comprising calcia/hafnia stabilized zirconia wherein the calcia is present from 3 to 10% by weight and the hafnia is present from 0.5 to 6% by weight.

18 Claims, 2 Drawing Sheets

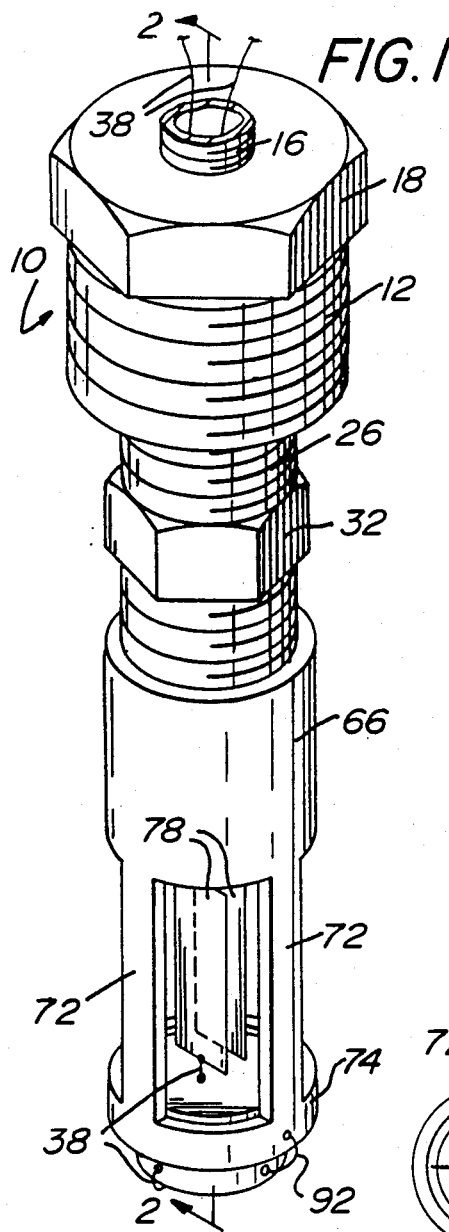
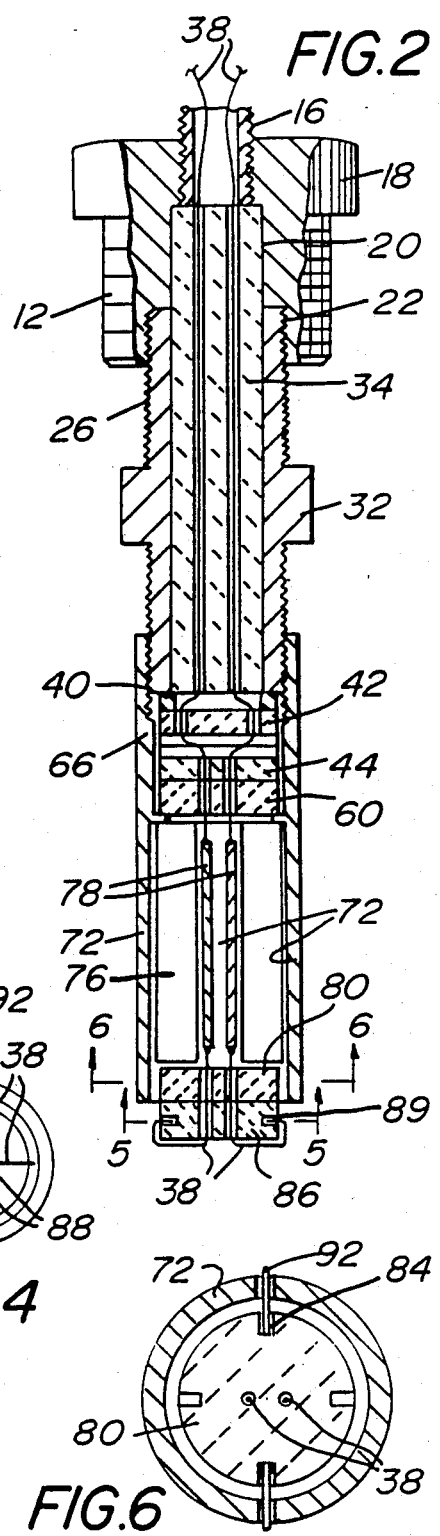
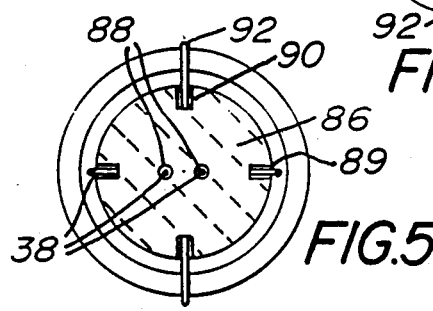
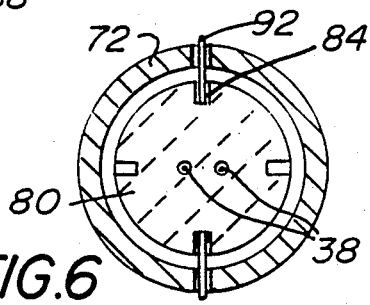

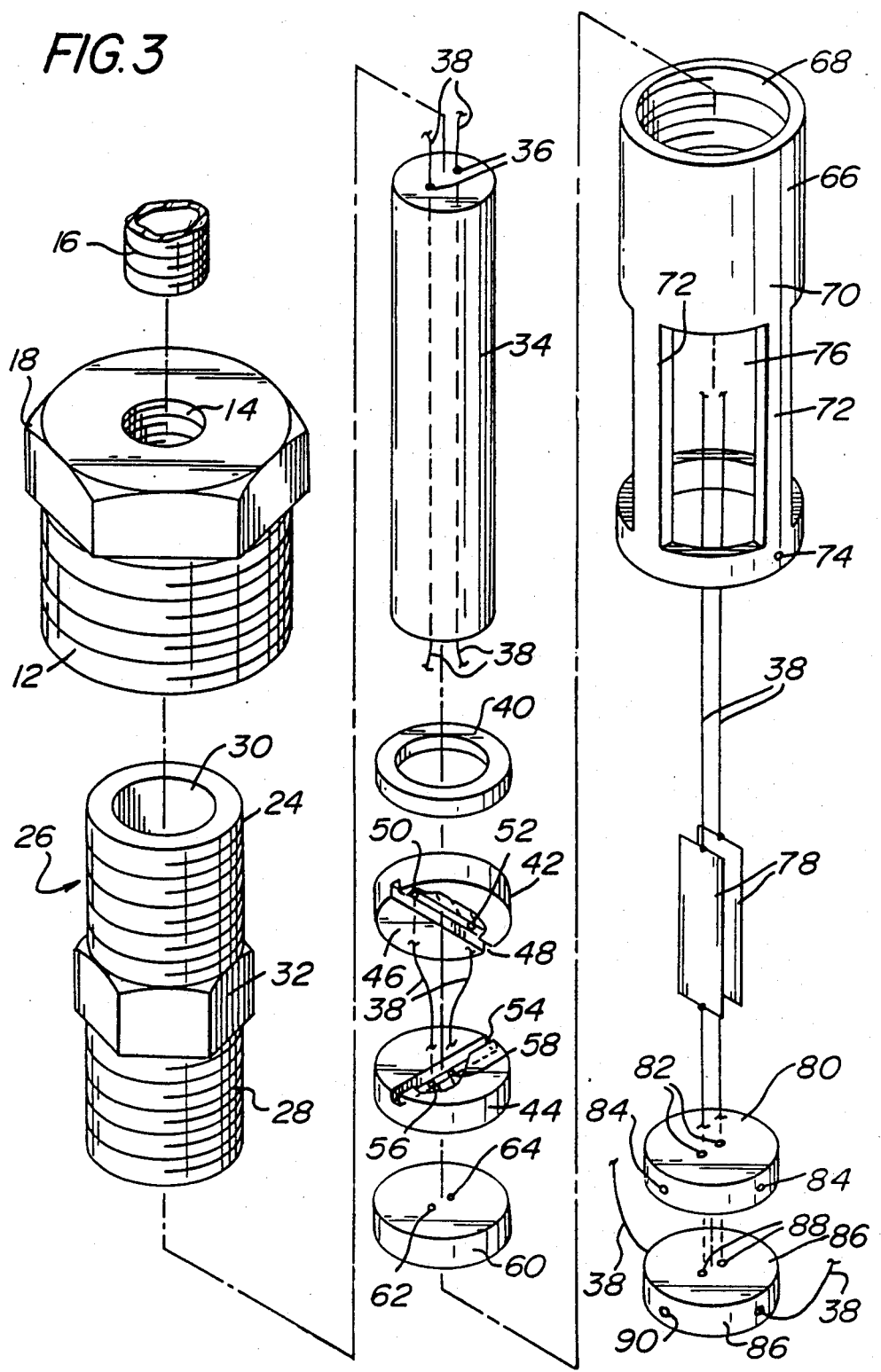

ELECTRODE ASSEMBLY FOR IN-SITU MEASUREMENT OF ELECTROLYTIC CONDUCTIVITY OF BOILER WATER

Field of the Invention

This invention relates generally to an electrode, and a method of electrically insulating the electrode, which is chemically, and hydrothermally, inert enough to be useful for in situ measurement of the electrolytic conductivity of boiler water, and/or any other neutral or alkaline aqueous solution at elevated temperature and/or pressure conditions, where other conductance electrodes, and methods of electrically insulating them, tend to become unsuitable. The electrode of the present invention in its preferred form consists of two parallel plates of platinum, each plate brazed with gold to a platinum and iridium alloy lead wire, electrically insulated by a zirconia ceramic stabilized with calcia/hafnia.

BACKGROUND OF THE INVENTION

There are several criteria which a suitable high temperature conductivity electrode should meet. First, the cell constant should vary only slightly with temperature. Furthermore, the temperature dependence of the cell constant should be a well-defined and smoothly varying function. For these criteria to be met, there are certain properties which the electrode should have. For example, electrode geometry should change very slightly and predictably over a large temperature range (100–350°C.). In addition, electrode response should exhibit no thermal hysteresis. The electrode and the insulating material should be reasonably inert with regard to chemical reaction in aqueous alkaline solutions at elevated temperature.

Moreover, the electrode pair should not acquire a permanent residual polarization nor should the electrode pair become excessively polarized during the measurement cycle. This is assured when electrode response is very nearly independent of the frequency at which the measurement is made. There should be no significant potential drop across the electrode pair, except during the measurement cycle. In other words, the electrode, when immersed in a electrolytic solution, should not give rise to galvanic action in the solution.

Traditionally, the conductivity of boiler water has been used to provide an estimate of the dissolved ionic solids present in the boiler, which is, in turn, empirically correlated with the purity of steam exiting the boiler. Generally, the conductivity of boiler water is measured at temperatures much cooler than those experienced in the boiler. This practice is a result of the relative ease with which accurate measurements of the conductance can be made at lower (near ambient) temperatures. The ASME has established guidelines for this parameter, along with caveats concerning its use.

However, the effect of temperature on electrolytic conductivity is pronounced, especially in boiler waters where hydrolytic chemical species, both organic and inorganic, are present. The hydrolysis and dissociation reactions produce ionic species which contribute to the overall conductivity of the boiler water. These reactions exhibit equilibria which are also greatly affected by temperature, as is the dissociation equilibrium of water itself. Thus, measurement of electrolytic conductivity at the operating temperature of the boiler would provide a more accurate picture of the actual ionic condition of the boiler water.

In high purity (20–50 uS/cm), but alkaline, boiler water above ca. 600 psig (250° C.), it has been generally considered infeasible to accurately measure conductivity in situ. One of the principal difficulties encountered when attempting to make measurements under these conditions (i.e., alkaline aqueous solutions at elevated temperatures) is the susceptibility of ceramic materials used for electrical insulation of the electrode pair towards dissolution. Another problem, albeit less serious, arises from the practical working temperature limit (about 250° C.) of polytetrafluoroethylene, and other fluoropolymers, commonly used in the pressure seals.

Use of instrumentation, operating in situ in boiler systems, which is based on principles of electrolytic conductance is well-established. For example, there are liquid level controllers, high water alarms, and high dissolved solids alarms commonly found in boiler systems, which operate based on conductance principles. These devices are simply qualitative conductance detectors. On the other hand, the conductivity electrode of the present invention is capable of accurately measuring boiler water conductivity under operating conditions.

BACKGROUND ART

There is prior art which describes the use of zirconia in fabrication of electrodes. However, none has involved, or is related to, the use of calcia/hafnia, or other metal oxide, stabilized zirconia comprising an insulating support structure for conductance, or other electrodes, in boiler water, or other high temperature aqueous solutions under alkaline or neutral conditions.

For example, several U.S. patents describe the use of zirconia as a material for fabrication of support structures for various types of electrodes. U.S. Pat. No. 4,331,742 teaches the use of yttria stabilized zirconia in the form of a tubular body which comprises part of a solid electrolytic cell. This application takes advantage of the material's ionized gas conducting properties. U.S. Pat. No. 4,597,170 describes the use of an yttria stabilized zirconia support tube on which to coat an electronic conductor in the fabrication of an electrode. U.S. Pat. Nos. 4,598,028 and 4,598,467 teach the use of calcia and yttria stabilized zirconia is high strength porous sintered support materials for solid oxide electrolytes in an electrochemical cell. The high temperature applications described in the aforementioned patents specifically refer to solid or vapor phases.

There are many patents which teach the use of zirconia, either not stabilized, or stabilized with yttria, calcia, or magnesia, in electrochemical gas phase oxygen sensors (U.S. Pat. Nos. 3,400,054; 4,221,650; 4,354,912; 4,571,285; 4,572,208; 4,574,042; 4,581,501; 4,585,499; 4,591,422). In all of the cases covered by these patents, zirconia plays an active role in the electrochemistry. Thus, the area to which the foregoing patents apply is well outside thes cope of the present invention. Related to the use of zirconia in oxygen sensors are U.S. Pat. No. 4,583,937, which describes a combustion apparatus which uses an oxygen sensing probe comprised of zirconia, and U.S. Pat. No. 3,297,551, which covers the use of zirconia (stabilized with alkaline earth metal oxides) as an electrolytic component in an oxygen reference electrode for determining oxygen in fluids.

Several patents describe the use of zirconia (both stabilized and not stabilized) as components in electrolytic cells. Zirconia, in these inventions, is used as either a substrate for an electrode, e.g., the anode (U.S. Pat. Nos. 4,581,117; 4,584,084; 4,597,846), or as a component of the anode, such as a coating (U.S. Pat. Nos. 3,649,485; 3,977,958; 4,146,438; 4,187,155; 4,213,843). The electrolytic cells, e.g., alkali metal/chlorine, are related to conductivity electrode pairs, but the zirconia in the electrodes of the electrolytic cells serves a completely different function and is used as a polarizable surface rather than as an electrical insulator (as for the conductivity electrode pair).

Zirconia has also been used as a solid electrolyte in fuel cells (U.S. Pat. Nos. 3,416,967 and 3,578,502), as a dielectric for semiconductor devices (U.S. Pat. No. 4,495,219), and as a film between two electrodes in a humidity indicating apparatus (U.S. Pat. No. 2,609,688).

BRIEF DESCRIPTION OF THE DRAWINGS

Reference is now made to the drawings wherein:

FIG. 1 is a three dimensional view showing an embodiment of the electrode assembly of the present invention;

FIG. 2 is a sectional view of the electrode assembly of FIG. 1 taken along the lines 2—2 of FIG. 1;

FIG. 3 is an exploded three dimensional view of the electrode assembly of FIG. 1;

FIG. 4 is a bottom plan view of the electrode assembly; and

FIGS. 5 and 6 are sectional views taken respectively along the lines 5—5 and 6—6 of FIG. 2.

DETAILED DESCRIPTION OF THE INVENTION

Durability and chemical inertness, under boiler conditions, of the insulation material, which also serves as a support for the platinum plates, are two of the important factors which have been imparted to the novel electrode of the present invention. In a series of experiments, which involved subjecting various ceramic materials to alkaline solutions (pH 11 measured at 25° C.) at elevated temperatures (about 300° C.) for varying lengths of time (19 hours to 1 week), it was surprising to discover that zirconium oxide, stabilized with about 6% calcium oxide and 3% hafnium oxide, met the chemical inertness criterion. In addition, it was discovered that this criterion was also met by zirconium oxide stabilized with a mixture of about 1–3% magnesium oxide/1–2% hafnium oxide. This was unexpected in view of data obtained for some of the other candidate materials being considered for use as electrical insulation.

In these experiments, a piece of ceramic, whose weight varied from 0.5 to 20.0 grams, was cleaned with demineralized water in a sonic bath, rinsed, dried in an oven at 150° C. for about 1 hour, and allowed to cool in a dessicator. The test piece was then placed in a 2-liter capacity titanium pressure vessel containing about 1 liter of demineralized water which was adjusted to pH 11 using sodium hydroxide. The vessel was heated to 298° C. at 1200 psig (568° F.) for the specified time period. After the vessel was cooled, the pH of the solution was measured and the solution was analyzed for some of the principal elements which comprised the ceramic. The test piece was rinsed with demineralized water, dried at 150° C. for about an hour, allowed to cool, and weighed.

The results of the test are presented in Table I.

TABLE I

Hydrothermal Stability of Ceramic Insulators 298° C. and 1200 psig at pH (25° C.) 11

| Material | Geometry | Duration | Initial Weight (g) | % Wt Loss | pH Initial | pH Final | Solution Chemistry |
|---|---|---|---|---|---|---|---|
| Pyrolytic Boron Nitride | Rectangular Plate | 19 hrs | 0.4630 | 0.48 | 11.1 | 10.4 | 0.7 ppm B |
|  |  | 7 days | 0.4607 | 4.47 | 11.0 | 10.2 | 8.5 ppm B |
| Alumina (99.5%) | Disk | 19 hrs | 16.5907 | 0.35 | 11.0 | 10.2 | 26 ppm Al |
| Alumina (99.7%) | Rectangular Plate | 19 hrs | 20.9779 | 0.33 | 11.0 | 10.0 | 37 ppm Al |
| Alumina (99.9%) | Hollow Cylinder | 7 days | 8.8057 | 0.61 | 11.0 | 10.0 | 22 ppm Al |
| Zirconia (Yttria/Hafnia Stabilized) | Disk | 7 days | 0.6846 | 6.77 | 11.1 | 10.8 | .01 ppm Zr |
| Zirconia (Yttria Stabilized) | Cube (Fibrous Vacuum Formed) | 7 days | 14.8461 | Piece Crumbled | 11.0 | 10.4 | .02 ppm Zr |
| Zirconia (Calcia/Hafnia Stabilized) | Disk | 19 hrs | 1.3070 | 0.02 | 11.1 | 11.0 | .01 ppm Zr |
|  |  | 7 days | 1.3682 | 0.17 | 11.0 | 11.2 | .01 ppm Zr |
| Zirconia (Hafnia/Magnesia Stabilized) | Disk | 7 days | 0.6248 | 0.00 | 11.0 | 11.2 | .01 ppm Zr. |
| Zirconia (Alumina/Calcia Stabilized) | Crucible | 7 days | 20.523 | 0.09 | 11.0 | 10.2 | 0.01 ppm Zr |

Although other insulating materials had been subjected to these test conditions, only those which exhibit some degree of chemical or structural stability under the conditions (i.e., alkaline water at 300° C. and 1200 psig) are given in Table I. Of these materials, calcia/hafnia stabilized (6%/3%) and hafnia/magnesia stabilized (2%/1%) zirconia exhibited exceptional stability over the other materials in Table I, based on weight loss and pH change. In fact, the calcia/hafnia stabilized and the hafnia/magnesia stabilized zirconia outperformed high purity alumina (99.9%) in the one-week test by a factor of greater than 3½ with respect to weight loss. The calcia/hafnia stabilized and the hafnia/magnesia stabilized zirconia were also the only materials which exhibited a pH change of only 0.2 unit, in contrast to, for example, the yttria stabilized zirconia, which exhibited a pH change of 0.3 unit. (It should be pointed out that the next smallest pH change was 0.8 unit observed for alumina/calcia stabilized zirconia, alumina and boron nitride.) The stability of calcia/hafnia stabilized and hafnia/magnesia stabilized zirconia in high temperature alkaline solutions is all the more remarkable in view of the results for the very closely related yttria stabilized and alumina/calcia stabilized zirconia.

The calcia/hafnia stabilized zirconia, for example, possesses the chemical and structural stability for fabrication of a reliable support structure for a high temperature conductivity electrode, but it also exhibits a very low electrical conductance at boiler temperatures. The electrical conductance is, at most, a few umhos/cm at the highest practical solution temperature (i.e., 375° C.) where the conductivity electrode support/housing would be useful. Thus, although the material does conduct electricity to a small degree, it is still sufficiently insulating, compared to the conductance of the platinum electrodes and the solutions to be measured. Calcia/hafnia stabilized zirconia also possesses a linear expansion coefficient of $10.9 \times 10^{-6}/K$ in the temperature range of interest, which is very near that of platinum ($9 \times 10^{-6}/K$). This is important when considering the effects of electrode geometry as a function of temperature.

It has been determined that pure zirconia is not satisfactory since it is not sufficiently chemically inert.

Accordingly, the addition of calcia/hafnia or hafnia/magnesia to stabilize the zirconia is necessary. It has been determined that the preferred amount of calcia will range between 3 and 10%, with 6% being the much preferred amount and the preferred amount of hafnia will range between 0.5 and 6%, with 3% being the much preferred amount in the calcia/hafnia stabilized zirconia. It has been determined that if the amount of calcia, or the amount of hafnia, significantly exceeds 10% by weight, the resulting composition may be a conductor of electricity to an unsatisfactory degree. If has also been determined that the preferred amount of hafnia will range between 0.5 and 4%, with 2% being the much preferred amount and the preferred amount of magnesia will range between 0.5 and 4%, with 1.5% being the much preferred amount in the hafnia/magnesia stabilized zirconia.

DETAILED DESCRIPTION OF FIGURES OF DRAWING

Reference is now made with figures of the drawings which show the physical aspects of the electrode assembly of the present invention utilizing in the preferred embodiment of calcia stabilized (5%) zirconia.

As can be best seen in any one of the FIGS. 1, 2 and 3, the electrode 10 comprises a reducing bushing 12 which has a threaded central opening or bore 14 to receive electrically insulated top fitting 16. The reducing bushing 12 also has a hex-shaped upper boss 18 for tightening purposes. Reducing bushing 12 possess a somewhat larger diameter central opening 20 (FIG. 2) which communicates with upper bore 14. There is an even larger internal lower opening 22 at the lower end of bushing 12 which communicates with the central opening 20 (FIG. 2). The larger internal lower opening 22 is threaded and receives the upper end 24 of adapter 26 which possess complimentary external threads that are received in the threaded lower opening 22 as can be best seen in FIG. 2. The adapter 26 also possesses a threaded lower end 28, a central hex-shaped boss 32 for tightening purposes and a through unthreaded opening 30 that receives an alumina insulator 34. As best seen in FIG. 3, the alumina insulator is basically a solid cylinder having longitudinal through openings 36 that will enable the passage of platinum based conductors or leads 38 as will be discussed hereinafter.

Positioned against the lower surface of the alumina insulator 34 is a teflon gasket 40 to provide a separation cushing for the pair of slotted discs 42 and 44 (FIG. 3) which are of the calcia stabilized zirconia already discussed hereinabove and therefore have important heat and electrical insulating properties.

The upper slotted disc 42 possesses adjacent its lower surface 46, a transverse slot 48 (FIG. 3) in the base of which are formed openings 50 and 52 to permit passage of the leads 38. The lower slotted disc 44 lies flush against the upper slotted disc 42 with the lower slotted disc 44 having the same details of construction of the upper slotted disc 42. Thus, the lower slotted disc 44 possesses a transverse slot 54 as well as openings 56 and 58. The openings 56 and 58, like openings 50 and 52 in upper disc 42 permit the passage of the leads 38. As shown in FIG. 2, the transverse slots 48 and 54 of the upper and lower discs 42 and 44 are aligned together to provide a combined transverse passage. The purpose of this combined transverse passage is to permit a transition zone that enables the leads 38 passing through somewhat widely spaced openings 50 and 52 in upper disc 42 to then pass through more closely spaced openings 56 and 58 in lower disc 44.

Positioned against the lower surface of the lower slotted disc 44 is a solid calcia stabilized zirconia disc 60, which possesses through holes 62 and 64 which again, permit passage of the leads 38.

A housing 66 is provided having a threaded upper interior surface 68 in head 70. The housing 66 is secured to the lower end 28 of adapter 26 by engagement of the threads formed externally in the lower end 28 with the internal threads 68 of the housing 66.

As also shown in FIGS. 1, 2 and 3, the housing 66 further includes depending legs 72 which terminate in a lower ring 74, with the depending legs 72 defining a plate receiving chamber 76 which houses platinum based plates 78.

Finally, substantially identical lower discs 80 and 86 are provided, with the two discs being of calcia stabilized zirconia. The upper disc 80 possesses through openings 82 and the lower disc 86 possesses through openings 88 for passage of leads 38. The lower disc 86 posesses a first pair of side taps 89 which receive for anchoring purposes the ends of the leads 38 as best shown in FIG. 2.

The lower disc 86 also possesses a second pair of side taps 90 which are offset 90° from the first pair of side taps. The upper disc 80 possesses a pair of side taps 84 which are aligned immediately above the second pair of side taps 90 from lower disc 86 as can be best seen in FIG. 3. The pairs of side taps 84 and 90 are to receive respectively each end of the length of non-conducting wire 92 for purposes of securing the discs 80 and 86 together and to the housing.

As can be seen best in FIG. 1, the overall assembly enables the plates or electrodes 78 to be readily accessible to extremely hot boiler water. In this way, certain physical constants of the boiler water such as conductivity, can be measured in a conventional way through electrical signals sent back through the leads 38 to measurement equipment at a remote location.

The housing 66 may be of a conventional corrosion resistant stainless steel with the plates 78 being spaced thin platinum electrodes anchored in place by the lower sections of the leads 38 and held away from housing 66 to avoid any shorting. As can be seen in FIG. 2, the slotted discs 42 and 44 and the solid disc 60 coupled with the gasket 40, prevent encroachment of the corrosive boiler water upwardly into and beyond the alumina insulator 34. The discs 80 and 86 provide an anchoring base for the lower ends of the leads 38. The discs 80 and 86 are also of calcia stabilized zirconia which functions as an electrical insulator. Thus, the measurement of the physical constants through the use of electrodes 78 is not distorted by the presence of the discs 80 and 86 or of the other discs which are of the calcia stabilized zirconia. Therefore, these discs have the necessary insulating properties to faithfully insulate a signal being generated or passed by the plates 78 upwardly through the leads 38 and to the various measurement equipment and such discs are not affected by the high temperature boiler water.

Calibration

After constructing and platinizing the electrode pair, a pretreatment procedure is required to remove impurities which may contaminate solutions used during calibration procedures. The electrode is fitted into the head of a pressure vessel by means of a compression fitting. The pressure vessel is then filled with demineralized water, sealed, and subsequently heated to 325° C. for one hour. Once the vessel is cooled, the electrode is thoroughly rinsed with high purity water (i.e., having a conductivity at 25° C. of <1 umho).

The calibration of the electrode, that is, determination of the cell constant, is performed at various temperature in a pressure vessel containing an aqueous solution prepared from a precisely weighed quantity of potassium chloride (0.01000 N or 0.7456 g KCl/kg). After thermal equilibrium at the desired temperature is attained, the conductance of the soliution is measured with the electrode. The cell constant is calculated by dividing the specific conductance of the solution (determined from reference values of the equivalent conductance of potassium chloride) by the measured conductance of the solution.

The results of such a calibration procedure for an electrode having zirconia housing/insulation are compared with those for an electrode of similar design but having PTFE (polytetrafluoroethylene) housing/insulation are given in the following table.

TABLE II

Cell Constants of Conductivity Electrodes at Various Temperatures

| Temperature °C. | Cell Constant (Housing/Insulation Material) | |
|---|---|---|
| | PTFE | CaO/HfO2-stabilized Zirconia |
| 25 | 0.0360 ± 0.0000 | 0.0391 ± 0.0002 |
| 100 | 0.0368 ± 0.0003 | 0.0402 ± 0.0003 |
| 200 | 0.0392 ± 0.0004 | 0.0419 ± 0.0001 |
| 250 | 0.0405 ± 0.0002 | — |
| 300 | 0.0403 | 0.0429 ± 0.0002 |

Over the calibration temperature range, the zirconia-housed electrode exhibited an average thermal coefficient of 0.0098% per degree C, whereas the expansion of the PTFE-housed electrode resulted in an increase in the cell constant of 0.054% per degree C. Thermal expansion over the 275-degree range results in a 7.1% change in the cell constant for the zirconia-housed electrode (compared to a 3% excepted change calculated on the basis of cell geometry). The PTFE-housed electrode exhibited a change in the cell constant of 12.5% over the same range (compared to a 14.9% change expected from cell geometry calculations using a linear thermal expansion coefficient of $55 \times 10^{-6}/K$).

ABSENCE OF THERMAL HYSTERESIS

Thermal hysteresis of the electrode response because of irreversible geometrical chnages in the dimensions of the housing/support material during heating/cooling cycles has not been observed when zirconia is used. For example, cell constants were determined at room temperature (25° C.) for a zirconia-housed electrode and a PTFE-housed electrode. The electrodes were then subjected to 335° C. (@2000 psig) for two hours in a pressure vessel containing demineralized water. The cell constants were determined again after the vessel and its contents were cooled to room temperature. The results are given in the following table.

TABLE III

Cell Constants of Conductivity Electrodes After Hydrothermal Treatment for 2 Hours at 335° C.

| | Cell Constant at 25° C. | |
|---|---|---|
| Electrode Housing | Before Treatment | After Treatment |
| PTFE | 0.0353 | 0.0389 |
| CaO/HfO2-stabilized Zirconia | 0.0370 | 0.0369 |

The results in Table III indicate that the thermal hysteresis observed for the zirconia-housed electrode was no greater than 0.2%, which is insignificant in view of the precision with which the cell constant can be determined (cf. Table II). This was not case for the PTFE-housed electrode.

OTHER CONSIDERATIONS

The variation of the electrode response with the oscillator frequency was investigated at several temperatures by measuring the conductance of a solution of potassium chloride at 25°, 126°, 200° and 300° C. using frequencies of 60 Hz, 1 kHz, and 3 kHz. The results are presented in Table IIIA.

TABLE III A

Conductance of 4 mM Aqueous KCl (at 25 C.) Measured with High Temperature Conductance Electrode as a Function of Frequency

| Temperature (C.) | Conductance (in uS) at | | |
|---|---|---|---|
| | 80 Hz | 1000 Hz | 3000 Hz |
| 25 | 15800 | 16100 | 16400 |
| 126 | 48500 | 50800 | 52800 |
| 200 | 67500 | 69500 | 71500 |
| 300 | 71500 | 73700 | 75000 |

The relatively weak dependence of the conductance on the frequency indicates that the electrode pair does not become significantly polarized during measurement, even at the elevated temperatures experienced in boiler waters.

The potential across the electrode was also determined as a function of temperature in the potassium chloride solution using a high impedance voltmeter. At 25°, 126°, 200°, 300° C., the emf across the electrode pair was 0.5, 4.2, 1.4, and 2.5 millivolts, respectively. The measured potentials are extremely small and are not expected to perturb the chemistry near the electrodes during measurement of conductance. These small emf values arise from the small differences in potential among platinum, iridium, and gold.

The zirconia-housed electrode was further tested in a Research Boiler at 254° C. (600 psig) and at 304° C. (1300 psig) operating at about 15 cycles of concentration with demineralized water containing potassium chloride at concentrations of about 6 ppm used as boiler feedwater. After attainment of steady-state conditions in the boiler, the conductivity of the boiler water was measured using a zirconia-housed electrode and compared with the value which would be expected based on the equivalent conductance of KCl at the operating temperature of the boiler and the cycled feedwater concentration. The duration for each test was one week. (This length of time assured steady-state concentrations in the boiler water.) The results of the Research Boiler tests are given in the following table.

TABLE IV

High Temperature Conductivity in Research Boilers Containing Potassium Chloride

| Run # | ppm KCl in Feedwater | Cycles of Concentration | Calculated Conductivity (uS/cm) | Observed Conductivity (uS/cm) |
|---|---|---|---|---|
| 1 | 5.68 | 15.1 ± 0.4 | 835 ± 25 | 918 ± 5 |
| 2 | 5.84 | 14.4 | 816 | 839 ± 6 |
| 3 | 5.68 | 15.4 | 848 | 876 ± 6 |
| 4 | 6.00 | 15.0 ± 0.3 | 873 | 955 ± 13 |
| 5* | 5.80 | 12.6 ± 0.1 | 709 | 890 |

*Data for Run #5 obtained at 304° C. (1300 psig). All other data are for 254° C. (600 psig).

The calculated conductivities are consistently lower (by 3–9%, with the exception of the 304° C. run) than the values measured experimentally using the high temperature conductivity electrode. The difference between the observed and calculated boiler water conductivities provides an estimate of the contributions from other ions which were not intentionally added to the boiler. (These species can be referred to as "stray ions".) For example, after each run, the boiler water was analyzed for several species which could be expected to be present as contaminants from either the demineralized water used for boiler feed or the boiler body and associated equipment. No iron or calcium was found above the analytical detection limit of 50 ppb, nor was zirconium (with a detection limit of 10 ppb). However, silica was present at a concentration which averaged around 3 ppm (as silicon dioxide). In addition, boilder water pH values were observed to vary between 8 and 9 (determined at room temperature). This alkaline pH condition was believed to arise from hydrolytic species (perhaps silicates) in the feedwater or hydroxide-producing residuals on the boiler walls which were not completely removed by the cleaning procedure performed between runs. This is nearly sufficient to account for the differences between the experimental and calculated conductivities.

Note also that the lack of observable concentrations of calcium or zirconium in the boiler water (at least at the present detection limits) is indicative of the chemical inertness of the calcia/hafnia stabilized zirconia electrode housing/support insulator.

It can be seen from all of the foregoing that the present invention achieves the objective of providing an electrode which can be used to determine conductance with a high degree of accuracy and precision under temperature conditions encountered in high pressure (1500 psig) boilers. The present invention contemplates several ceramic materials for use as electrical insulation and/or mechanical support for an electrode. These materials were evaluated for hydrothermal stability under high temperature (298° C.) alkaline conditions (pH 11 at 25° C.). Once a suitable material was identified, a platinum conductance electrode for in situ measurement of boiler water conductance was constructed with a parallel-plate design having dimensions chosen to yield low cell constants, thereby increasing the sensitivity. The thermal and electrical characteristics of the electrode, and its response in solutions of standard electrolytes, were determined using static pressure vessels and the Research Boilers (at various temperature/pressure conditions to about 304° C./1300 psig for at lest one week).

In accordance with the present invention, the electrolytic conductance of boiler water can be measured accurately in situ, at least up to 304° C./1300 psig, to within about 1%, using the electrode of the present invention. This level of performance is suitable for monitoring boiler water treatment programs, especially under high purity feedwater conditions, using in situ conductance measurements. Also, the electrode of the present invention can be used to monitor other types of dynamic water, such as water in a geothermal system or wherever conductance of alkaline or neutral water at elevated temperatures and/or pressures must be determined.

Moreover, two zirconia-based materials have been found to exhibit sufficient hydrothermal stability under boiler conditions to be useful as electrical insulators and electrode support materials for the high temperature conductance electrode have been identified.

The cell constant of the conductance electrode has a smooth, well-defined temperature dependence and varies by an average of 0.05% per degree over the range 25–300 C. This facilitates highly accurate determination of the conductance for any temperature within this range.

In order to obtain reliable conductance values, it is necessary to coat the electrodes with a thin film of platinum black, which aids in the prevention of electrode polarization during measurement. Although the initial layers formed during platinization tend to erode under turbulent conditions, only enough film to result in a dull gray electrode surface is needed to ensure reliable determinations.

It is further contemplated within the scope of this invention that materials other than calcia/hafnia stabilized or hafnia/magnesia stabilized zirconia be used. For this reason, the expression "stabilized zirconia" is being employed in certain of the claims. For instance, other metal oxides, such as thoria or ceria may be used. However, the stabilized zirconia or other compounds of the present invention must be rated satisfactory under a test procedure for evaluating the hydrothermal stability of ceramic materials. This procedure involves the following 12 steps to determine whether a material is suitable for use as an insulator/support in the construction of a high temperature electrolytic conductance electrode for boiler water;

Step 1: For a test specimen, which may be of any geometry, weighing between about 0.5 to 20.0 grams, clean for 5 to 10 minutes in a sonic bath containing demineralized water, dry in an oven for about 1 hour at 150° C., and allow to cool in an inert (anhydrous) atmosphere.

Step 2: Weigh the test specimen, measure its physical dimensions, and determine the surface area (which will be exposed to the test conditions).

Step 3: Add the specimen to a pressure vessel (in this case, one constructed of titanium) containing 1 liter of demineralized water which has been adjusted to pH 11 through the addition of sodium hydroxide.

Step 4: Heat the vessel to about 300° C. at 1200 psig (572° F.) for 19 hours.

Step 5: Allow the vessel to cool to about 25° C. and measured the pH of the aqueous solution in the pressure vessel.

Step 6: Rinse the specimen with demineralized water, dry in an oven at 150° C. for 1 hour, and allow to cool in an anhydrous atmosphere, as before.

Step 7: Weigh the test specimen and calculate the weight as a percentage of the total initial weight, and calculate the weight loss in mg/sq cm.

Step 8: If the percentage weight loss calculated in the previous step is <1%, or if the weight loss per unit surface area is <5%, and if the pH change is about one-half pH unit or less, then the material may be suitable for use in the electrode. If the material may be suitable by this criterion, proceed to Step 10.

Step 9: If the percentage weight loss is >1%, or if the weight loss per unit surface area is >5%, and if the pH change is >one-half unit, then the material is definitely unsuitable for use in the electrode.

Step 10: (From Step 8) A fresh specimen with the same composition as that used in Steps 1 through 8 above, should be treated as per Steps 1 through 7 above, except that the duration of the exposure to elevated temperature/pH conditions in Step 4 will be about 7 days.

Step 11: If the percentage weight loss is <1%, or if the weight loss per unit surface area is <5%, and if the pH change is <one-half pH unit, then the material is suitable for electrode insulation in the construction of a precision conductance electrode for in situ measurement of boiler water conductivity.

Step 12: If the conditions of Step 1 are not met, then the material is definitely not suitable for use in electrode construction.

NOTE: The 19-hour test is suitable for culling unsatisfactory materials, but is not strictly necessary. If time is not a constraint, (i.e., because of equipment demands) then it is entirely prudent and satisfactory to begin the test procedure at Step 10, i.e., the 7-day test duration.

Reference is now made to the following Table V as showing the investigation of various materials as an insulator/support in the construction of a high temperature electrolytic conductance electrode for boiler water.

TABLE V

Suitability of Ceramics for Use in Construction of the in situ Boiler Water Conductance Electrode

| | Results After Step # in Test Procedure | | | |
|---|---|---|---|---|
| | Step #8 | | Step #11 | |
| Ceramic Material | Possibly Suitable | Not Suitable | Definitely Suitable | Definitely Not Suitable |
| 1. Pyrolytic Boron Nitride | X | — | — | X |
| 2. Hot-pressed Boron Nitride | — | X | — | — |
| 3. Conax Alumina | — | X | — | — |
| 4. 99.5% Alumina (Duramics) | — | X | — | — |
| 5. 99.7% Alumina (Alfa) | — | X | — | — |
| 6. 99.9% Alumina (Ampex) | — | — | — | X |
| 7. Ampex Alumina | — | — | — | X |
| 8. Aremcolox (Partially Fired) | — | X | — | — |
| 9. Aremcolox (Fully Fired) | — | X | — | — |
| 10. Calcia/Hafnia-Stabilized Zirconia (Alfa) | X | — | X | — |
| 11. Yttria-Stabilized Zirconia (Corning) | — | X | — | — |
| 12. Hafnia/Magnesia-Stabilized Zirconia Composition 1027 (Corning) | N/A | N/A | X | — |
| 13. Hafnia/Magnesia-Stabilized Zirconia Composition 5027 (Corning) | N/A | N/A | X | — |
| 14. Magnesia/Hafnia-Stabilized Zirconia Composition 1876 (Corning) | N/A | N/A | X | — |
| 15. Macor | — | X | — | — |
| 16. Mycalex | — | X | — | — |
| 17. Yttria/Hafnia | | | | |

TABLE V-continued

Suitability of Ceramics for Use in Construction of the in situ Boiler Water Conductance Electrode

| Ceramic Material | Results After Step # in Test Procedure | | | |
|---|---|---|---|---|
| | Step #8 | | Step #11 | |
| | Possibly Suitable | Not Suitable | Definitely Suitable | Definitely Not Suitable |
| Stabilized Zirconia (Zircar) | N/A | N/A | — | X |
| 18. Alumina/Calcia-Stabilized Zirconia (Alfa) | N/A | N/A | — | X |

An X in the column signifies a positive result. Only 7-day tests were performed for the Corning experimental zirconia formulations.

Without further elaboration, the foregoing will so fully illustrate our invention that others may, by applying future knowledge, adopt the same for use under various conditions of service.

What is claimed as the invention:

1. An electrode assembly for in situ measurement of physical constants of boiler water at elevated temperature and/or pressure and under variable boiler operating conditions wherein pH can vary between 7 and at least 11, said electrode assembly comprising electrodes supported by stabilized zirconia and wherein electrical current generated by said electrodes in contact with the boiler water is conducted by conductive leads supported by said stabilized zirconia, said zirconia being stabilized with about 6% calcia and 3% hafnia or about 1 to 3% magnesia and 1 to 2% hafnia.

2. The electrode assembly of claim 1 wherein said stabilized zirconia is sufficiently chemically and hydrothermally inert so as to be useful for in situ measurement of the electrical conductivity of boiler water at boiler conditions.

3. The electrode assembly of claim 2 wherein said stabilized zirconia has a low electrical conductance at boiler operating temperatures and also serves as a support for physical constant determination plates.

4. The electrode assembly of claim 3 wherein the physical constant determination plates are two parallel electrically conducting platinum plates to which are connected lengths of platinum and irridium alloy lead wire.

5. The electrode assembly of claim 1 comprising calcia stabilized zirconia wherein the zirconia is stabilized by calcia and hafnia which is present from 3 to 10% by weight.

6. The electrode assembly of claim 5 wherein the calcia is present in an amount of 6% by weight.

7. The electrode assembly of claim 6 wherein the calcia and hafnia stabilized zirconia has a linear coefficient of expansion similar to that of platinum.

8. The electrode assembly of claim 5 wherein the zirconia is stabilized with about 6% by weight calcia, 3% by weight hafnium oxide and traces of aluminum oxide.

9. The electrode assembly of claim 1 wherein the zirconia is stabilized by the presence of a sufficient amount of hafnia and magnesia to withstand the variable boiler operating conditions.

10. A method of insulating and using an electrode assembly for performing in situ measurement of physical constants of boiler water at elevated temperature and/or pressure, at variable boiler operating conditions wherein pH can vary between 7 and at least 11, said method comprising protecting and supporting electrodes of the assembly with stabilized zirconia, the electrodes of the assembly in said boiler water, transmitting electrical current generated by said electrodes by conductive leads supported by said stabilized zirconia, with said zirconia being stabilized with about 6% calcia and 3% hafnia or about 1 to 3% magnesia and 1 to 2% hafnia, and determining a value by reading the generated eletrical current passing through said electrodes.

11. The method of claim 10 wherein said stabilized zirconia is sufficiently chemically and hydrothermally inert so as to be useful for in situ measurement of the electrical conductivity of boiler water at boiler conditions.

12. The method of claim 11 wherein said stabilized zirconia has a low electrical conductance at boiler operating temperatures and also serves as a support for physical constant determination plates.

13. The method of claim 12 wherein there are two parallel electrically conducting platinum plates to which are connected lengths of platinum and iridium alloy lead wire.

14. The method of claim 10 comprising calcia stabilized zirconia wherein the zirconia is stabilized by calcia and hafnia which is present from 3 to 10% by weight.

15. The method of claim 14 wherein the calcia is present in an amount of 6% by weight.

16. The method of claim 15 wherein the calcia and hafnia stabilized zirconia has a linear coefficient of expansion similar to that of platinum.

17. The method of claim 14 wherein the zirconia is stabilized with about 6% by weight calcia, 3% by weight hafnium oxide and traces of aluminum oxide.

18. The method of claim 10 wherein the zirconia is stabilized by the presence of a sufficient amount of hafnia and magnesia to withstand the variable boiler operating conditions.

* * * * *

UNITED STATES PATENT AND TRADEMARK OFFICE
CERTIFICATE OF CORRECTION

PATENT NO. : 4,883,566
DATED : November 28, 1989
INVENTOR(S) : Muccitelli et al

It is certified that error appears in the above-identified patent and that said Letters Patent is hereby corrected as shown below:

Col. 12, line 17, please delete "Step 1" and substitute therefor --- Step 11 ---.

Signed and Sealed this

Second Day of April, 1991

Attest:

Attesting Officer

HARRY F. MANBECK, JR.

Commissioner of Patents and Trademarks